(12) United States Patent
Gronlund et al.

(10) Patent No.: US 8,895,929 B2
(45) Date of Patent: Nov. 25, 2014

(54) ANALYSIS OF SUBSTRATES HAVING AGENTS DEPOSITED THEREON

(71) Applicant: Colgate-Palmolive Company, New York, NY (US)

(72) Inventors: Jennifer Gronlund, Flemington, NJ (US); Guofeng Xu, Plainsboro, NJ (US); Deborah A. Peru, Lebanon, NJ (US); Ravi Subramanyam, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/322,897

(22) Filed: Jul. 2, 2014

(65) Prior Publication Data

US 2014/0312232 A1    Oct. 23, 2014

Related U.S. Application Data

(63) Continuation of application No. 12/936,324, filed as application No. PCT/US2009/039651 on Apr. 6, 2009, now Pat. No. 8,803,095.

(60) Provisional application No. 61/042,558, filed on Apr. 4, 2008.

(51) Int. Cl.
  *G01J 5/02* (2006.01)
  *G01N 21/33* (2006.01)
  *G01N 21/35* (2014.01)

(52) U.S. Cl.
  CPC .............. *G01N 21/33* (2013.01); *G01N 21/359* (2013.01)
  USPC ................. 250/339.08; 250/339.07; 250/372; 600/432

(58) Field of Classification Search
  CPC .......................................................... G01J 3/42
  USPC ................. 250/339.07, 372, 339.08; 600/432
  See application file for complete search history.

(56) References Cited

U.S. PATENT DOCUMENTS

| 5,051,359 A | 9/1991 | Characklis |
| 5,197,470 A | 3/1993 | Helfer et al. |

(Continued)

FOREIGN PATENT DOCUMENTS

| CN | 1299646 C | 2/2005 |
| CN | 1905835 A | 1/2007 |

(Continued)

OTHER PUBLICATIONS

Barkvoll P. et al: "Studies on the interaction between sodium lauryl sulfate and hydroxyapatite using Fourier transformed infrared spectroscopy" Journal de Biologie Buccale, Jun. 1988, 16(2): 75-79, XP008108021.

(Continued)

*Primary Examiner* — Christine Sung
(74) *Attorney, Agent, or Firm* — Howard C. Lee

(57) ABSTRACT

Improved analytical, diagnostic, monitoring, and other methods (and their associated devices) for evaluating the extent of deposition of an agent onto a substrate are described. Exemplary methods may be used in the in the monitoring of the dental health of patients or in the fast, efficient screening and/or characterization of formulations in terms of their use for depositing oral actives onto tooth surfaces. The methods involve the direct or in situ analysis of substrates, onto which agents are deposited, using Near-IR spectroscopy and/or UV spectroscopy.

15 Claims, 15 Drawing Sheets

(56) References Cited

U.S. PATENT DOCUMENTS

| | | |
|---|---|---|
| 5,368,845 A | 11/1994 | Gaffar et al. |
| 5,976,508 A | 11/1999 | Nabi et al. |
| 6,135,774 A | 10/2000 | Hack et al. |
| 6,303,081 B1 | 10/2001 | Mink et al. |
| 6,309,835 B1 | 10/2001 | Iyer et al. |
| 6,934,576 B2 | 8/2005 | Camacho et al. |
| 7,167,742 B2 | 1/2007 | Camacho et al. |
| 7,862,335 B2 | 1/2011 | Berube-Lauziere et al. |
| 2002/0107448 A1 | 8/2002 | Gandjbakhche et al. |
| 2002/0127143 A1 | 9/2002 | Kuo |
| 2002/0193671 A1 | 12/2002 | Ciurczak et al. |
| 2004/0071594 A1 | 4/2004 | Malone et al. |
| 2005/0130321 A1 | 6/2005 | Nicholson et al. |
| 2006/0044555 A1 | 3/2006 | Wang et al. |
| 2006/0280650 A1 | 12/2006 | Wong et al. |
| 2007/0237726 A1 | 10/2007 | White et al. |
| 2008/0177481 A1 | 7/2008 | Popp et al. |
| 2009/0306543 A1 | 12/2009 | Slowey et al. |

FOREIGN PATENT DOCUMENTS

| | | |
|---|---|---|
| DE | 10 2006 048271 | 3/2008 |
| EP | 0750901 | 1/1997 |
| EP | 1055457 | 11/2000 |
| EP | 1455268 | 9/2004 |
| JP | 08-026953 | 1/1996 |
| JP | 09-509739 | 9/1997 |
| JP | 2003-508748 | 3/2003 |
| JP | 2003-511148 | 3/2003 |
| JP | 2009-216497 | 9/2009 |
| KR | 2009-0090914 | 8/2009 |
| RU | 2170079 | 7/2001 |
| RU | 64515 | 7/2007 |
| WO | WO 97/10800 | 3/1997 |
| WO | WO 01/51012 | 7/2001 |
| WO | WO 2005/023146 | 3/2005 |
| WO | WO 2005/099404 | 10/2005 |
| WO | WO 2007/123880 | 11/2007 |

OTHER PUBLICATIONS

Foss Dispersive Near IR Mode XDS with Rapid Content Analyzer (RCA), http://www.foss-5nirsystem.com/rca.html, retrieved from internet Aug. 27, 2012.

Fukuda et al., 2003, "Bonding efficacy of polyalkenoic acids to hydroxyapatite, enamel and dentin," Biomaterials 24(11):1861-1867.

Gotz et al., "Effects of elevated hydrogen peroxide 'strip' bleaching on surface and subsurface enamel including subsurface histomorphology, micro-chemical composition and fluorescence changes" 2007, Journal of Dentistry, 35:457-466.

Haluko J. L. et al.: "Direct Analysis of Triclosan Deposition on Hydroxyapatite by Spectroscopic Methods" Apr. 4, 2008, XP007909108, Retrieved from the Internet: URL http://iadr.confex.com/iadr/2008Dallas/techprogram/abstract_101188.htm> [retrieved on Jul. 1, 2009].

Hedzelek et al., "Infrared Spectroscopic Identifcation of Chosen Dental Materials and Natural Teeth," 2008, Proceedings of the Meeting of Synchrotron Radiation Users, 114:471-484.

International Search Report and Written Opinion for International Application No. PCT/US2009/039651 mailed on Jul. 20, 2009.

International Search Report in International Application No. PCT/US2010/061708 mailed Apr. 20, 2011.

Jordan et al., 2000, "The Analysis ofTriclosan in Toothpaste via LC/FT-IR Mobile Phase Elimination AN-20," The Analysis of Triclosan in Toothpaste, 22, Department of Chemistry, 6 Virginia Polytechnic Institute and State University, Blacksburg, VA 24061.

Kimetach et al., 1997, "Methods of Sample Preparing for Investigation by Fourier Transform IR Spectroscopy Methodological Recommendations," Methodological Recommendations by Standing Committee for Narcotics Control, Record No. 1/55-97.

Son et al., 2007, "Effects of Ultraviolet Intensity and Wavelength on the Photolysis ofTriclosan," 7 Water Science Technology 55(1-2):209-216.

| Sample | Triclosan Deposited, ppm |
|---|---|
| Delivery System 1, Disk 1 | 30.7 |
| Delivery System 1, Disk 2 | 35.0 |
| Delivery System 1, Disk 3 | 35.1 |
| Delivery System 2, Disk 1 | 94.3 |
| Delivery System 2, Disk 2 | 80.0 |
| Delivery System 2, Disk 3 | 85.1 |

FIG. 5

ANALYSIS OF SUBSTRATES HAVING AGENTS DEPOSITED THEREON

CROSS-REFERENCE TO RELATED PATENT APPLICATIONS

The present application is a continuation of U.S. application Ser. No. 12/936,324, filed Oct. 4, 2010, which is a national stage entry under 35 U.S.C. §371 of International Patent Application No. PCT/US2009/039651, filed Apr. 6, 2009, which in turn claims the benefit of U.S. Provisional Patent Application No. 61/042,558, filed Apr. 4, 2008, the entireties of which are hereby incorporated by reference.

FIELD OF THE INVENTION

The present invention relates to methods and devices for measuring the extent of deposition or uptake of agents (e.g., oral active agents) onto substrates (e.g., hydroxyapatite surfaces to mimic tooth surfaces). The amount or concentration of an agent may be efficiently determined on a substrate (e.g., with the agent and substrate both in solid form), using Near-Infrared (Near-IR) spectroscopy or Ultraviolet (UV) spectroscopy.

BACKGROUND OF THE INVENTION

Conventional methods for analyzing the deposition of agents, such as oral active agents used in dental care, involve incubating the agent with a substrate, washing the incubated substrate, and then subjecting it to solvent extraction. Subsequently, the extract is analyzed using high-performance liquid chromatography (HPLC) to provide an indirect quantification of the deposited agent. In a particular type of such an analysis, oral active agents such as Triclosan, either in neat solutions or in dentifrice formulations, are incubated with saliva-coated hydroxyapatite disks used to model hard tissue substrates, prior to performing solvent extraction on the disk.

The solvent-extraction/HPLC method, however, has limitations. For example the method robes on the indirect analysis of an extract rather than the direct analysis of the surface onto which the agent is deposited. As a result of the extraction and subsequent HPLC steps, the analysis often takes considerable time. Moreover, the method relies on the use of an extracting agent which may not always be compatible with a given agent/substrate system (e.g., may decompose or adversely affect, for example by reaction with, the agent to be analyzed or otherwise influence the form of the agent).

Therefore, a need exists in the art for methods that can efficiently analyze or characterize the rate or amount of deposition of an agent onto a substrate. Ideally, such methods can be performed via direct analysis of the agent/substrate system and provide fast results.

BRIEF SUMMARY OF THE INVENTION

The invention relates to efficient, reliable methods such as screening methods for characterizing the deposition of agents (e.g., oral active agents) onto surfaces. Such methods can be used to assess and compare different formulations comprising the agent to be deposited, as well as different delivery systems for the agent. The methods are also applicable for evaluation or diagnostic purposes in patients or other users, and can therefore be applied to in vivo systems, for example, in the analysis of deposition of an oral active agent onto the tooth surface of a patient. The methods are also suitable for personal use, for example, in the case of a user desiring to monitor the effectiveness of a particular dental care regimen.

The direct methods described herein can be used to obtain an analytical result in a relatively short time, for example on the order of minutes (e.g., 5-10 minutes) or even seconds (e.g., less than 60 seconds or 10-45 seconds). The analytical methods, according to some embodiments, determine the distribution of various agents about a surface, for example, they may be used to determine whether or not they are uniformly distributed.

Accordingly, aspects of the invention relate to a method for measuring deposition of an oral agent such as an oral care active on a substrate. The method comprises contacting the substrate with the oral agent to deposit an amount of the oral agent thereon, and analyzing the substrate using Near-Infrared (Near-IR) spectroscopy or Ultraviolet (UV) spectroscopy.

Other aspects of the invention relate to a method of diagnosing the oral condition of a patient. The method comprises measuring the presence of an oral agent in a patient sample using Near-Infrared (Near-IR) spectroscopy or Ultraviolet (UV) spectroscopy.

Other aspects of the invention relate to a method for evaluating the effectiveness of an oral delivery system. The method comprises depositing an oral agent onto a substrate using the dental instrument, and additionally analyzing the substrate using Near-Infrared (Near-IR) spectroscopy or Ultraviolet (UV) spectroscopy to measure the extent of deposition.

Other aspects of the invention relate to devices or instruments for performing any of the above methods.

Other aspects of the invention relate to one or more tangible computer readable media storing executable instructions that, when executed, cause a data processing system to perform a method comprising steps of analyzing a Near-IR spectrum or a UV spectrum generated according to the methods described above, using a mathematical method is selected from the group consisting of first and second derivative, peak area integration, partial least squares regression (PLS), Kubelka-Munk conversion, multiple linear regression, and spectral subtraction (e.g., to subtract background signals).

The methods and devices above can be used in the absolute measurement of amounts or concentrations of agents deposited onto a substrate. Alternatively, the methods may be used to obtain relative amounts or concentrations of these agents (e.g., in the case a monitoring application). The methods may be used to compare the extent of deposition of an agent as a function of its concentration in an initial composition (e.g., in a dentifrice used to incubate to substrate according to methods described herein), as a function of the use of differing delivery systems (e.g., a paste versus a gel system), or as a function of any of a number of other parameters that will be appreciated by those having skill in the art, having regard for the present disclosure.

These and other aspects of the invention will become apparent from the following Detailed Description.

BRIEF DESCRIPTION OF THE DRAWINGS

A more complete understanding of the present invention and the advantages thereof may be acquired by referring to the following description in consideration of the accompanying drawings, which should be understood to present an illustration of various aspects of the invention and/or principles involved, and wherein:

FIG. 5 depicts the data obtained during validation of the Near-IR analysis method;

DETAILED DESCRIPTION OF THE INVENTION

Figure 1:
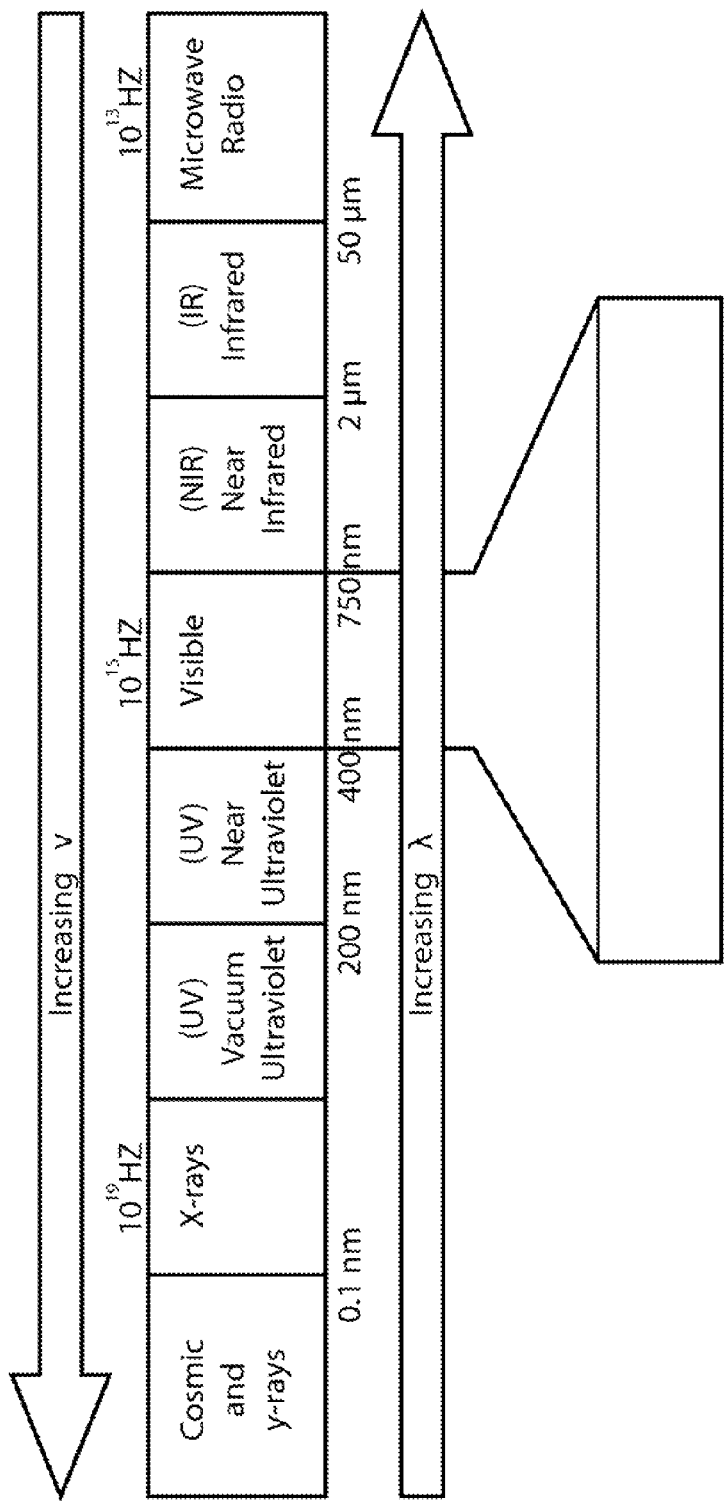
FIG. 1 is an illustration of the electromagnetic spectrum, including suitable wavelengths for use in Near-IR or UV spectroscopy.
Figure 2:
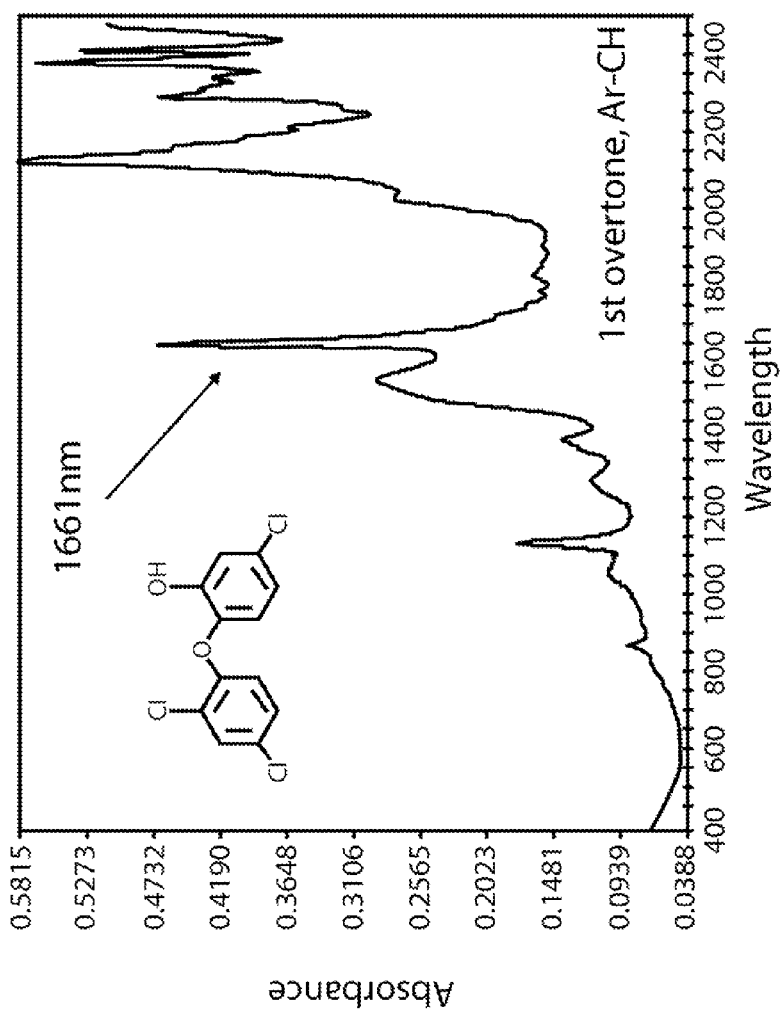
FIG. 2 is a Near-IR spectrum, showing the "fingerprint" of the oral active agent, Triclosan.
Figure 3:
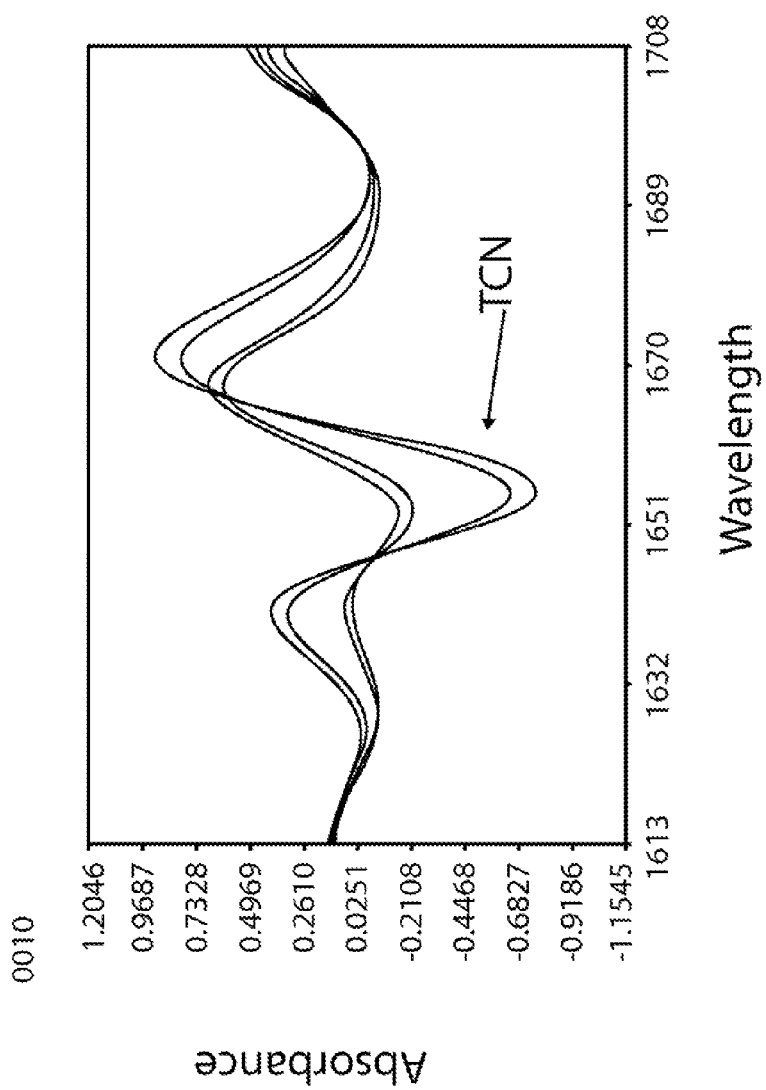
FIG. 3 is the $2^{nd}$ derivative of a Near-IR spectrum of Triclosan.
Figure 4:
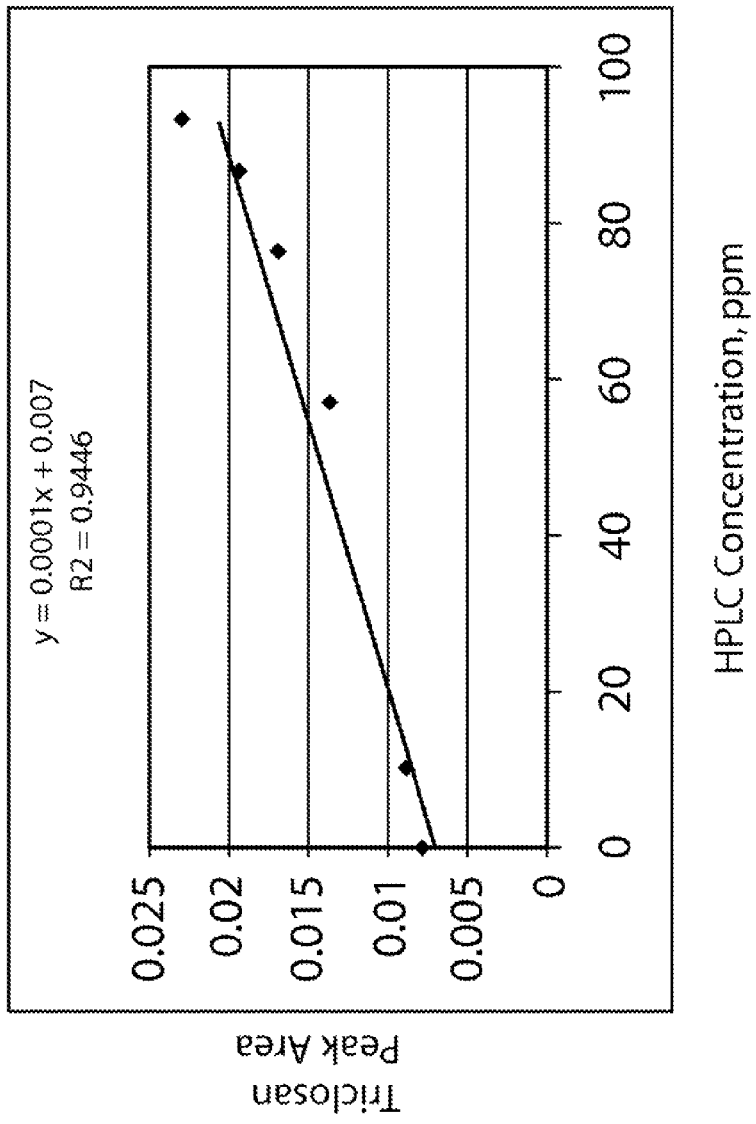
FIG. 4 depicts the relationship between the Triclosan peak area, measured using Near-IR, and the Triclosan concentration (in ppm) measured using HPLC.
Figure 6:
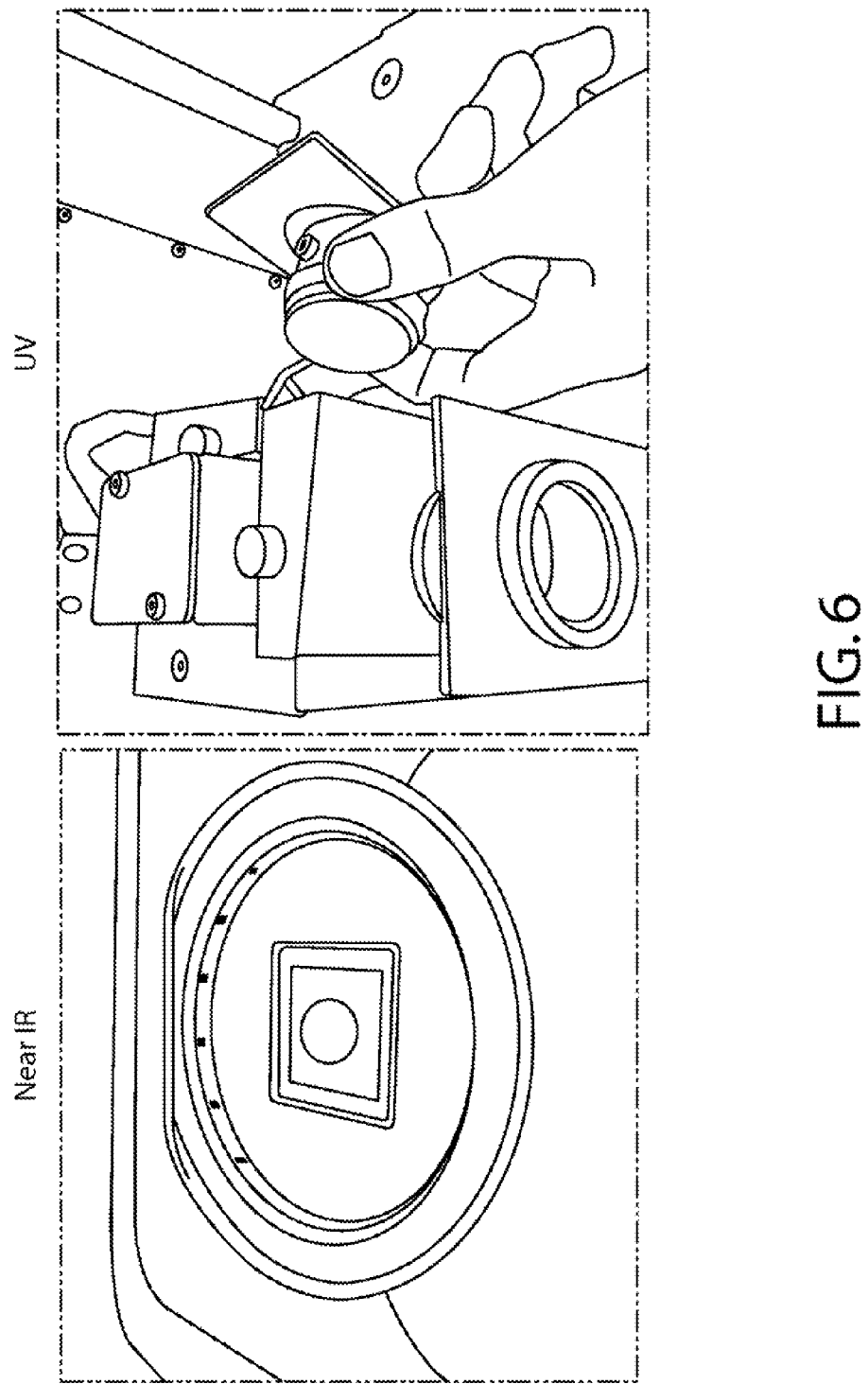
FIG. 6 depicts an experimental step in which HAP disks an introduced into Near-IR or UV spectrometers.
Figure 7:
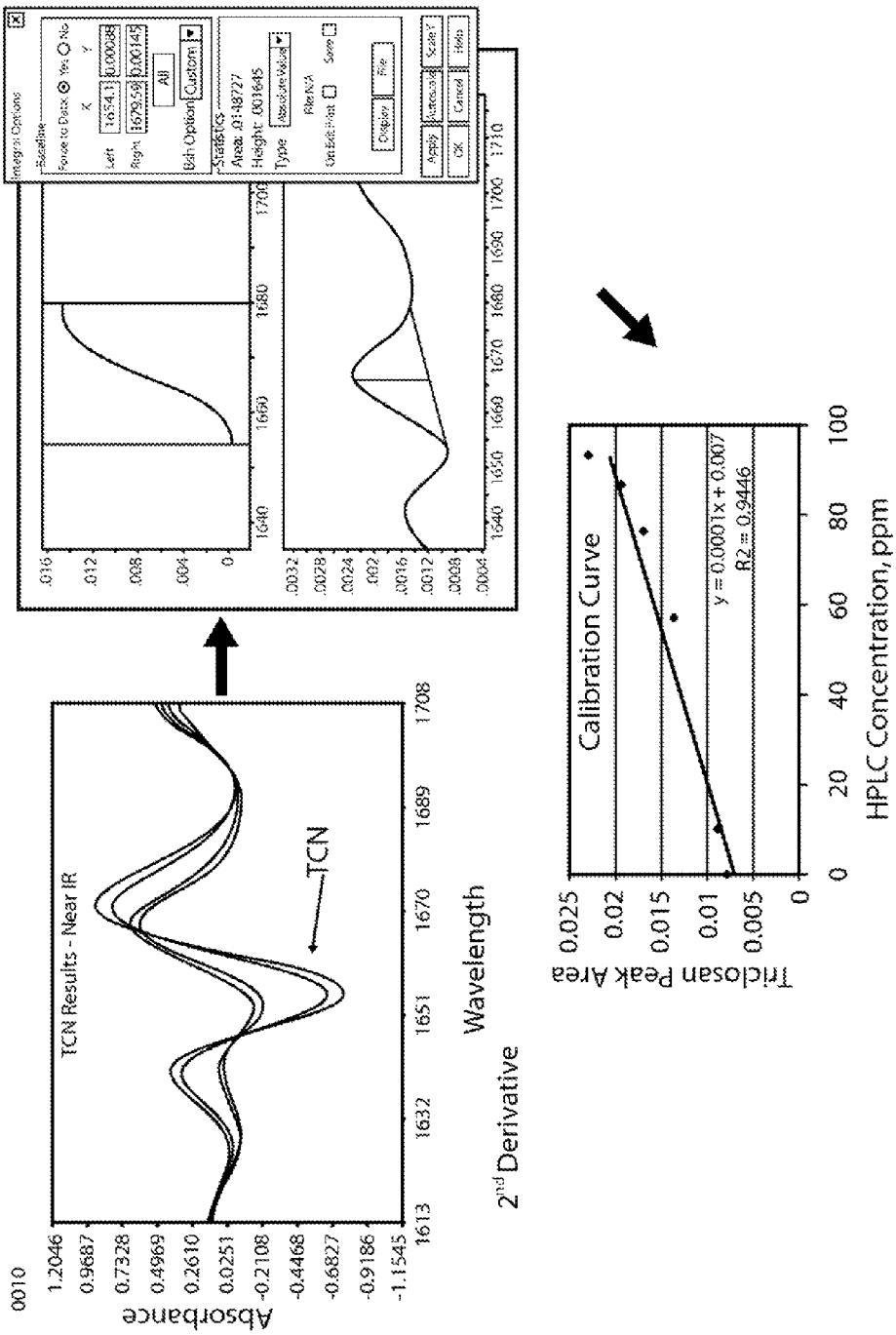
FIG. 7 depicts a process whereby Near-IR analytical methods are correlated with conventional solvent extraction/HPLC methods.
Figure 8:
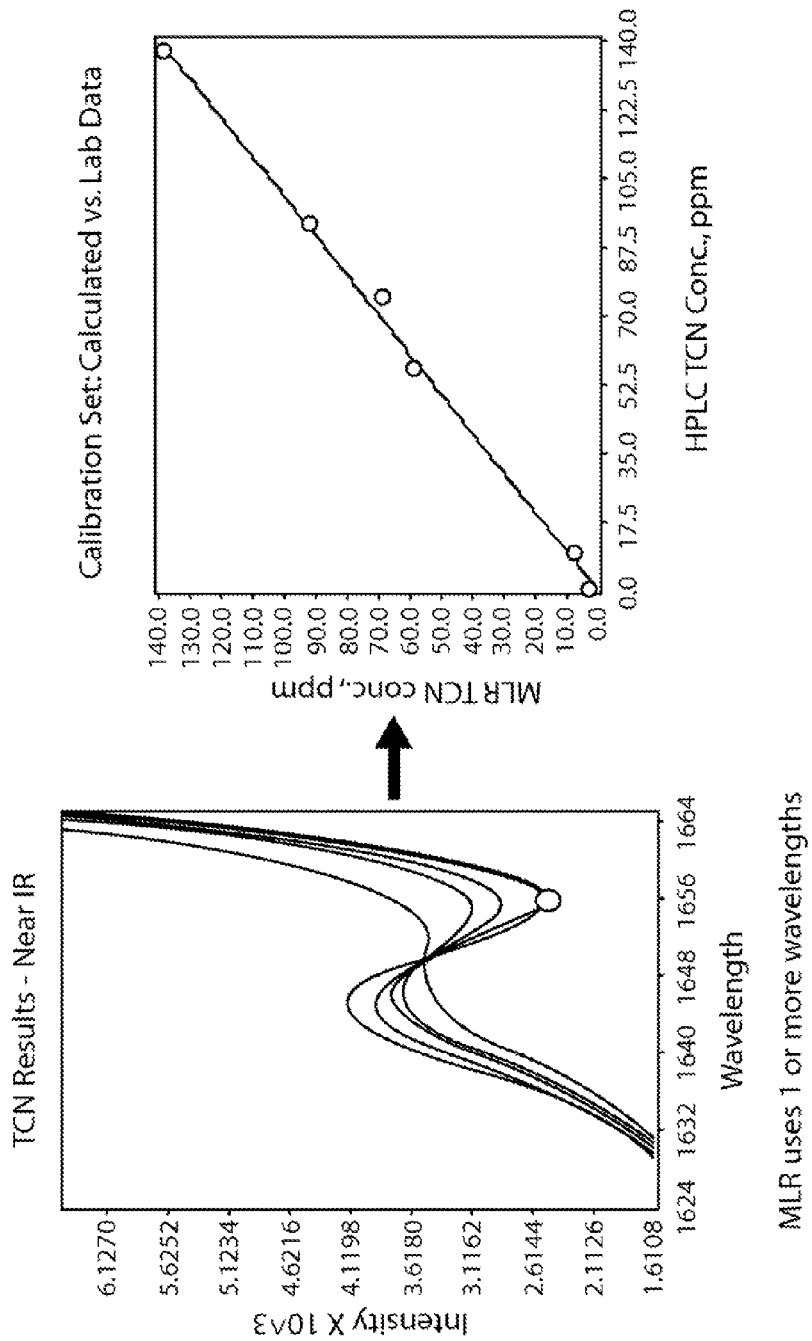
FIG. 8 depicts the use of data analysis techniques in correlating a Near-IR analytical methods with conventional solvent extraction/HPLC methods.
Figure 9:
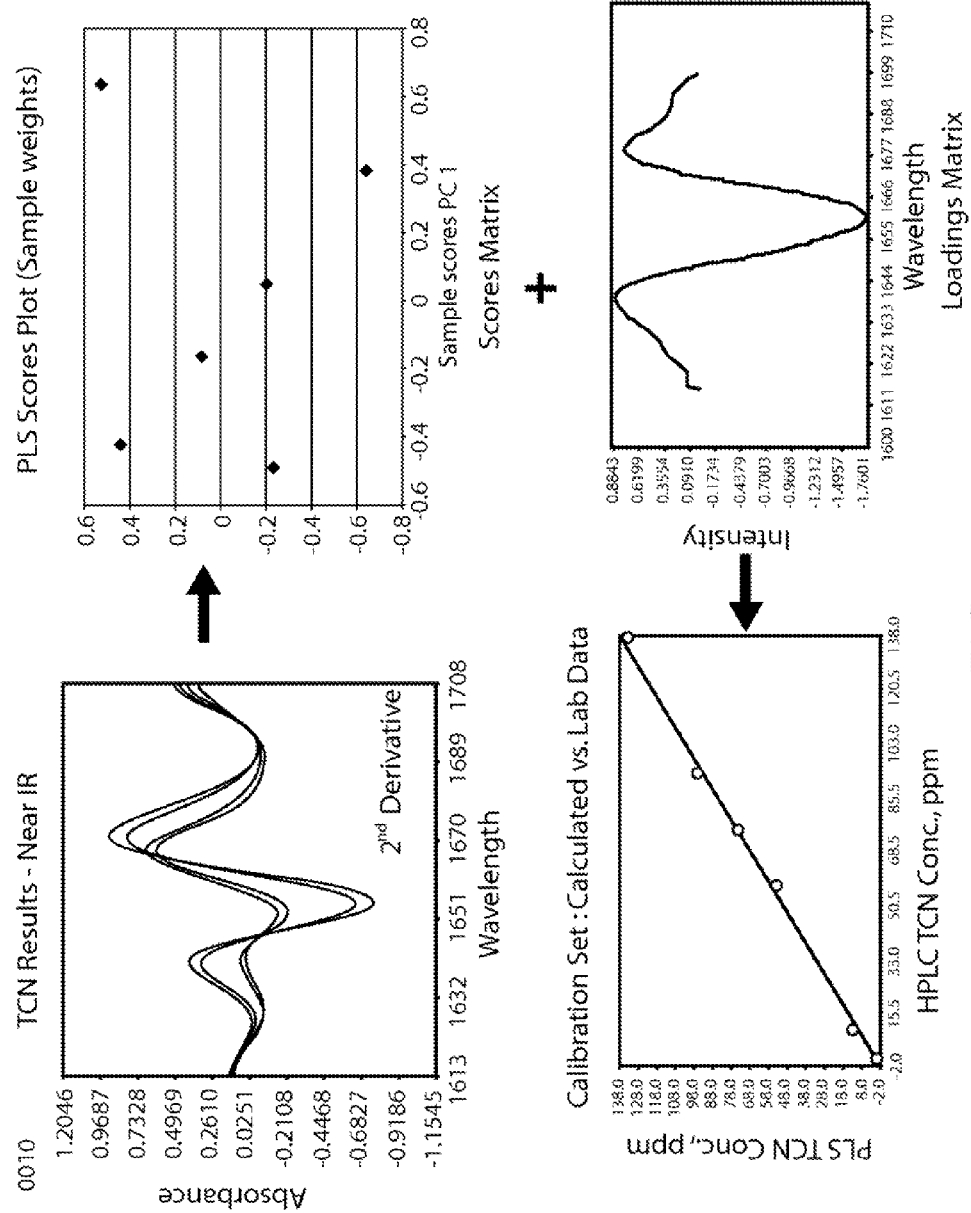
FIG. 9 depicts the use of data analysis techniques, including partial least squares regression, in correlating a Near-IR analytical methods with conventional solvent extraction/HPLC methods.
Figure 10:
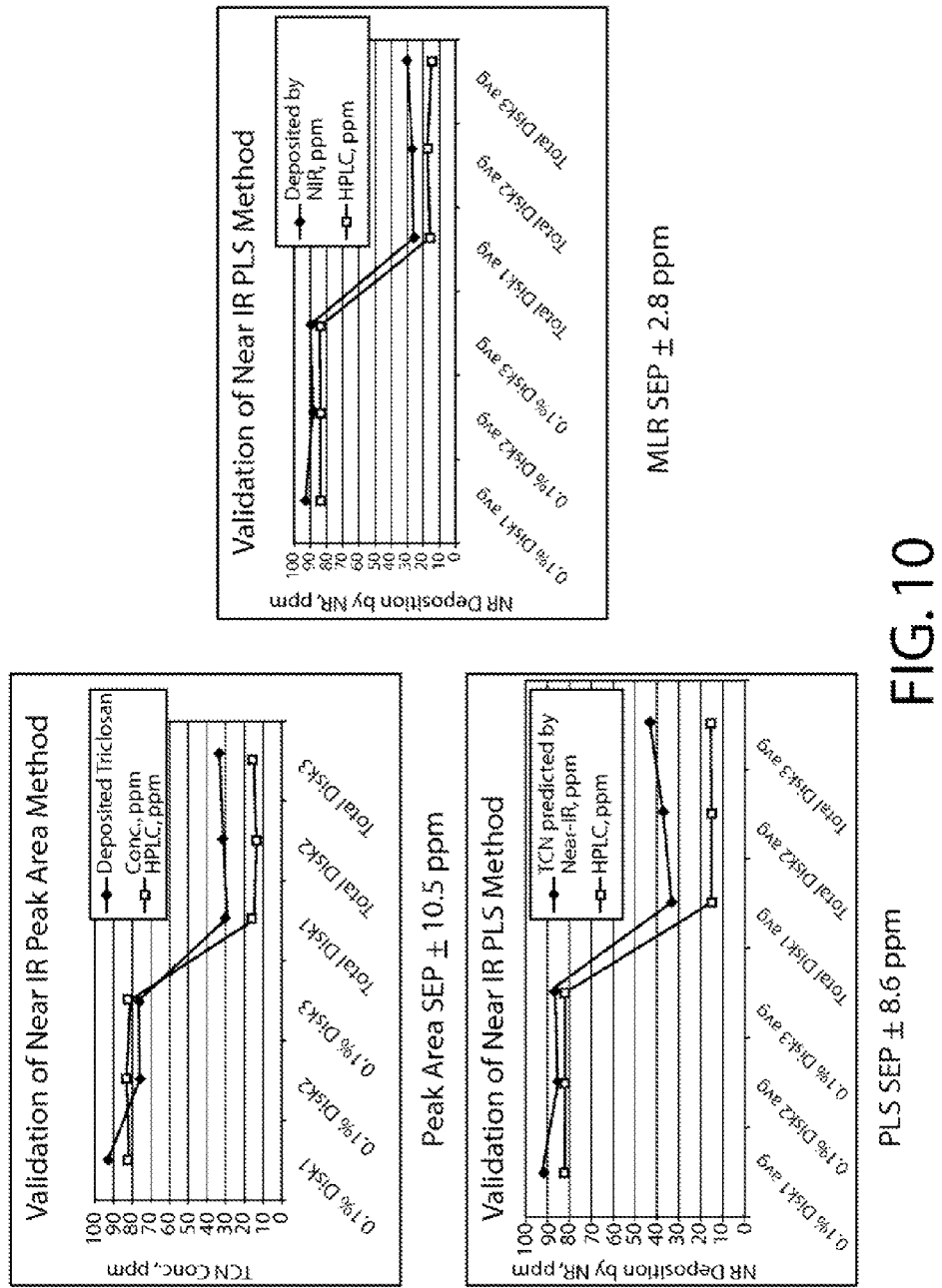
FIG. 10 depicts the use of data analysis techniques, including partial least squares regression and multiple linear regression, in correlating a Near-IR analytical methods with conventional solvent extraction/HPLC methods.
Figure 11:
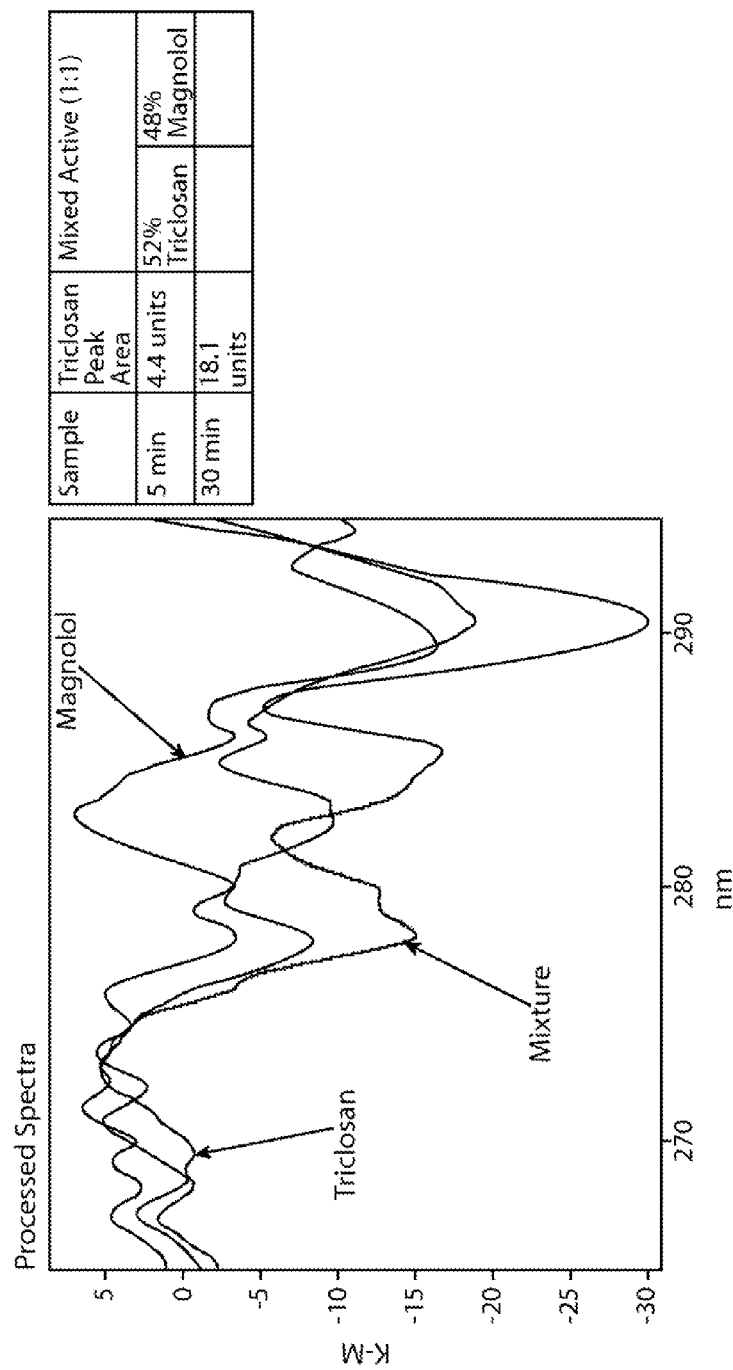
FIG. 11 depicts a UV spectrum for a mixture of two components, obtained using UV spectroscopy, with the spectrometer modified with an integrating sphere accessory.
Figure 12:
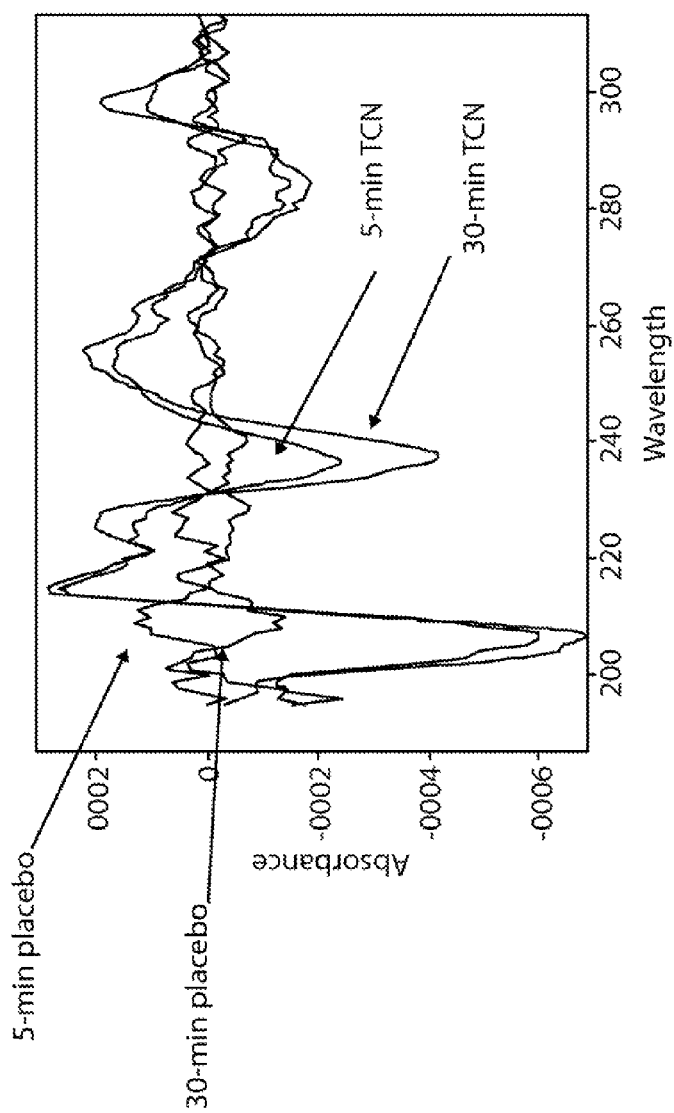
FIG. 12 depicts UV spectra for various samples, including placebo samples and substrates incubated with Triclosan for 5 minutes and 30 minutes.

Aspects of the invention relate to methods and devices for the detection of agents (e.g., oral agents) that have been delivered and deposited onto a substrate (e.g., a substrate in the oral cavity such as a tooth or soft tissue). Other substrates include bodily fluids such as blood and saliva, which may be analyzed according to methods described herein for analyzing the uptake or deposition of agents (e.g., pharmaceutical compounds). The methods allow the quantification of the amount of uptake of the agent by the substrate and consequently these methods are useful, for example, in comparing the uptake rates and/or total amount of agent deposited under varying conditions. The methods are also useful in characterizing the nature of interaction between the agent and the substrate.

Agents such as oral agents include those used in oral care and/or those used as model oral agents. Examples include phosphates, amino acids, potassium salts, and stannous compounds. Triclosan and sodium lauryl sulfate are representative examples of active agents used in oral care. In the case of oral agents, they may be used in the methods and devices as pure compounds, but are often in the form of solution with an aqueous or organic solvent. Solutions are typically physiologically acceptable, in order to best simulate the conditions of actual use. Oral agents may also be in the form of a dentifrice such as a paste, gel, or slurry.

The agents are generally brought into contact with a substrate, such that the resulting agent-containing substrate can be analyzed using methods discussed herein to determine the agent uptake or deposition onto the substrate. In the case of oral agents, a commonly-employed substrate is a hydroxyapatite (HAP) sample, such as a HAP disk used to model a tooth surface. For example, a saliva-coated HAP disk (sc-HAP) may be treated or contacted with the oral agent under conditions which result in the deposition of at least some of the oral agent onto the substrate. "Saliva" can refer to natural saliva or, alternatively, saliva that is purified and/or otherwise processed, or even synthetic saliva designed to mimic the performance of natural saliva for purposes of an analysis.

According to other embodiments, the substrate can be the actual tissue, for example, the tooth or soft tissue of a dental patient or dentrifrice user desiring knowledge of the extent of deposition of an oral agent onto the tooth surface. The information nay be relevant to the care of the patient administered by an oral care professional or administered by the patient himself/herself.

In a representative embodiment, a substrate such as a scHAP disk is treated or contacted with an oral agent such as Triclosan in the form of a liquid dentrifrice solution or a dentrifrice slurry. The resulting agent-containing substrate (i.e., having the oral agent deposited thereon) is then analyzed using Near-IR spectroscopy or UV spectroscopy, or a combination of these methods. Results of these analyses show that the deposition can be accurately measured, based on a comparison with conventional methods involving solvent extraction, which are significantly more cumbersome and time-consuming.

In other embodiments, the methods described herein are applicable for diagnosing an oral condition (e.g., the deposition of an oral active agent, the deposition of a biofilm, or the extent of tooth whitening or tooth gloss), including the progress of an oral treatment regimen (e.g., to improve oral health, whiten teeth, or provide tooth gloss) in a patient. In still other embodiments, the method is applicable to determining the effectiveness of an oral care delivery system. Devices for performing these methods are also contemplated, having complexities that vary according to their intended use. For example, while laboratory devices may have the capability to analyze absorbance (or reflection) over an extended range of wavelengths, a simpler device used by a dental professional may have a more limited capability and measure absorbance only at distinct wavelengths or wavelength ranges that are characteristic of an oral agent/substrate system of interest (e.g., a particular oral active/tooth system).

Even simpler devices are applicable for home use by a consumer to monitor, for example, an ongoing oral treatment regimen by determining relative amounts of deposited agents over time. Such devices may be used alone or may alternatively be incorporated into toothbrushes or other oral care devices. Users of the device will advantageously be able to obtain quick results to allow effective monitoring of an oral care regimen. Also, users can respond to such results by adapting the regimen appropriately (e.g., by brushing and/or flossing more often or for a longer period).

In this manner, methods described herein will be useful for monitoring the extent, or trend over time, of a desired agent (e.g., a beneficial, oral active agent such as Triclosan). The methods are also applicable, however, to the characterization of deposited, undesired agents such as detrimental tooth film buildup which may be countered by an appropriate response. The methods may be combined with other methods such as fluorescence, if necessary to adequately characterize a particular agent/substrate system.

Analysis of the substrate, having agent deposited thereon, is performed using Near-Infrared (Near-IR) spectroscopy of Ultraviolet (UV) spectroscopy. Generally, the spectroscopy instrument is adapted with accessories for solid measurement, in order to perform direct measurement (amount or concentration) of the agent deposited onto the substrate. In the case of a Near-IR spectroscopy instrument or a UV spectroscopy instrument, the solid measurement accessory can be a rapid content analyzer (RCA) or an integrating sphere, respectively. In the case of the integrating sphere, the sample of the agent-containing substrate to be analyzed may be positioned (e.g., centrally positioned using a light beam) onto a reflective disk plate, such as a white ceramic plate commercially available under the name Spectralon®.

A representative technique for preparing the substrate sample, onto which the agent has been deposited, involves drying this sample, for example to predetermined water concentration to minimize sample-to-sample variations in the results which are not due to the parameter being studied. Representative parameters to be studied include changes in the amount of agent deposited under controlled conditions, as a function of either (i) the agent concentration, such as the agent concentration initially present in a solution or dentifrice composition, or (ii) the concentration of agent delivery enhancers or agent delivery retardants (e.g., initial concentrations in such solutions or dentifrice compositions).

The Near-IR or UV analysis of the agent-containing sample (sample onto which at least a portion of the agent initially present, for example, in a solution or dentifrice) results in the generation of a corresponding spectrum (e.g., Near-IR spectrum or UV spectrum) that is characterized by the relationship between the sample absorbance and the wavelength used. In the case of a UV spectrum (e.g., obtained using an integrating sphere as a solid measurement accessory), the initial spectrum may be characterized by reflection vs. wavelength. These reflection values may, however, be converted to a corresponding absorbance spectrum by performing conversion operations such as a Kubelka-Munk conversion.

In the case of either Near-IR or UV spectra obtained from analysis according to the methods described herein, it is often desired to subtract a background or reference signal due to materials such as known additives present in solution with the agent. Thus, data analysis methods often require performing spectral subtraction to better resolve the spectrum of the agent of interest (e.g., to obtain a resolved spectrum, by subtracting a reference spectrum such as that obtained from saliva alone). Additional data manipulation techniques that are advantageously performed include determining first or second derivatives of the Near-IR or UV spectra (which may be converted, in the case of UV, and/or resolved as described above) to improve the peak clarity (e.g., by distinguishing the sample peaks from interfering peaks). Once peak clarity is resolved to a desired extent using these (and optionally other data manipulation techniques), the areas under various relevant, resulting peaks may be determined by integration, with the areas corresponding to concentrations or absolute amounts of deposited agents of interest.

In some embodiments, other data manipulation techniques may be used to reduce the extent of interfering peaks, for example those obtained from materials such as additives, impurities, or even additional agents whose deposition or uptake is to be measured using the methods described herein. In the case of a mixture of deposited agents, for example, multiple linear regression or partial least squares regression may be useful for correcting for interference or overlap of peaks from the different agents in the mixture.

The wavelengths used in the Near-IR and UV analysis methods described herein may be fairly broad wavelength ranges over a portion of the electromagnetic spectrum. These wavelengths may be in the UV vacuum wavelength range, the near UV range, the visible light range, the Near-IR range, and/or the IR range. Often, it will be desired to tailor the wavelengths (or wavelength ranges) used for analysis to those that are specific to a particular agent or agent/excipient combination (i.e., those wavelengths that are characteristically absorbed or reflected by the analyzing radiation, and can be thus used to "fingerprint" the agent of interest).

The selection of only the most pertinent wavelengths (e.g., only 3 or 4, characteristic wavelengths) for a given system can be beneficial in reducing the complexity and/or cost of the spectroscopy instrument. The selection process of wavelengths for use in the analysis can be based, for example, on a linear regression or least squares analysis of the integrated peak area about a candidate wavelength, with respect to the concentration of the agent, as measured in various calibration samples (i.e., containing known or reference amounts of agent). The selection methodology may also involve the determination of absorption wavelengths that are unique to a particular agent of interest (e.g., based on a spectrum obtained from a pure solution or pure powdered form of the agent) or have minimal overlap with peaks of other materials. Using selection processes, for example, it has been determined that suitable wavelengths for the Near-IR analysis of Triclosan include those in the ranges of 1604-1804 nm and 2190-2300 nm. Suitable wavelengths for the Near-IR analysis of the oral active agent, sodium lauryl sulfate, include those in the ranges of 1192-2198 nm, 1626-1814 nm, and 2250-2400 nm. Suitable wavelengths using UV analysis include those in the range of 200-500 nm.

Near-IR and UV/V can be used separately or even in combination to obtain desired information about the delivery of agents such as oral active agents, key ingredients, and additives such as excipients. According to some embodiments, Near-IR analysis can provide a total amount of deposited agents and UV analysis can determine concentrations of individual components in a mixture of agents or a mixture of one or more agents and one or more additives.

The methods and devices described herein thus provide a number of possible advantages in various applications. For example, the methods are useful in the development of rapid analytical methods for direct quantification of active delivery on oral surface models. Representative methods allow the direct measurement of the deposition of oral active agents on HAP substrates. The methods are additionally useful for examining oral active agents in their native state in a dentifrice matrix and for assaying finished products in view of the present disclosure, it will be seen that other advantages may be achieved and other advantageous results may be obtained. It will also be appreciated that the methods and devices described above may be used with, or performed in conjunction with, conventional methods and devices. As various changes could be made in the above apparatuses and methods without departing from the scope of the present disclosure, it is intended that all matter contained in this application shall be interpreted as illustrative only.

Computer Data Processing Environment

Figure 13:
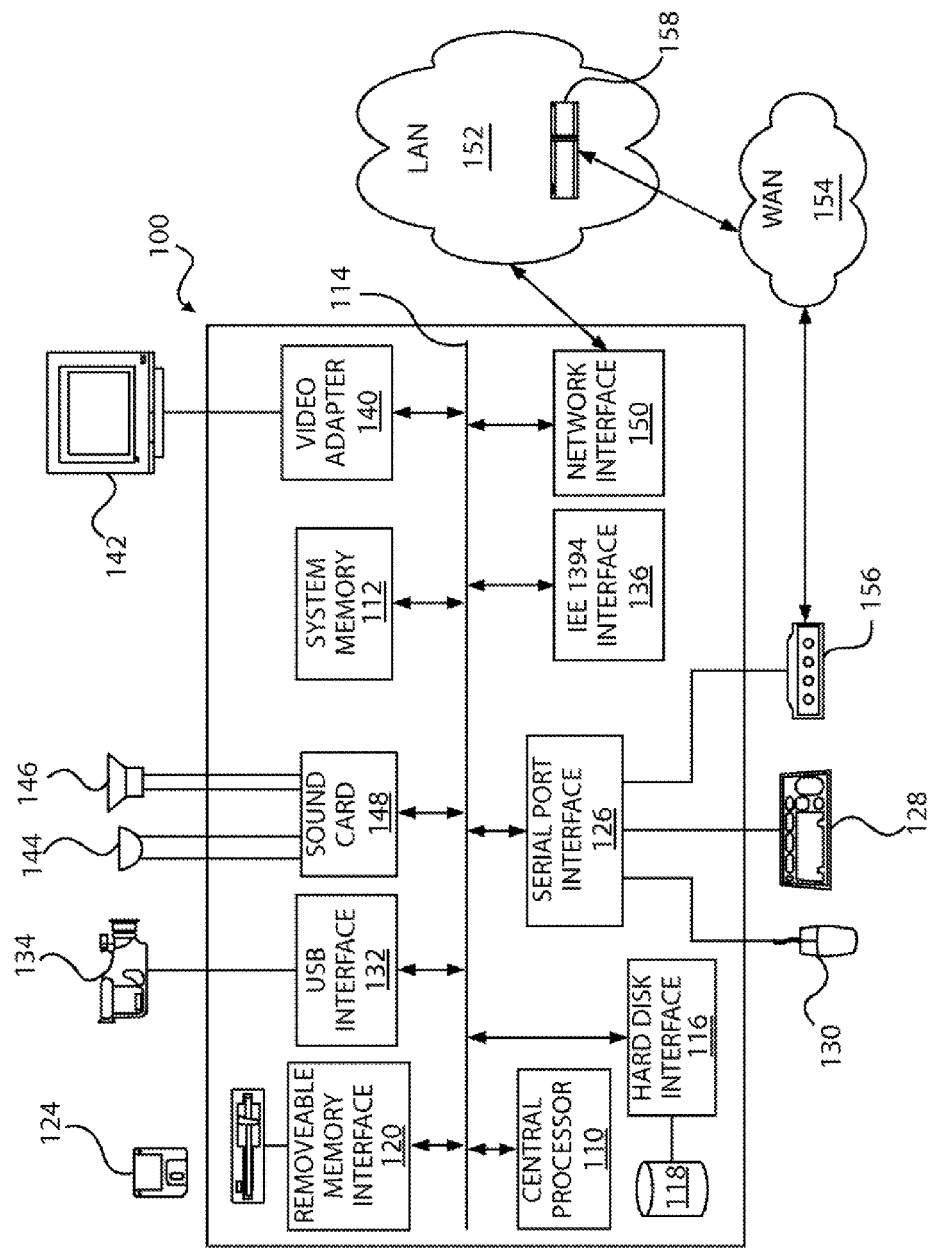
FIG. 13 illustrates a representative computer system environment embodying one or more aspects of the invention.

Various aspects of the present invention may be implemented in the context of data structure, program modules, program and computer instructions executed in a computer implemented environment. Thus, it is helpful to briefly discuss a general purpose computing environment. Accordingly, one or more aspects of the invention may be embodied in one or more computer systems, such as is illustrated in FIG. 13. In FIG. 13, computer 100 includes a central processor 110, a system memory 112 and a system bus 114 that couples various system components including the system memory 112 to the central processor unit 110. System bus 114 may be any of several types of bus structures including a memory bus or memory controller, a peripheral bus, and a local bus using any of a variety of bus architectures. The structure of system memory 112 is well known to those skilled in the art and may include a basic input/output system (BIOS) stored in a read only memory (ROM) and one or more program modules such as operating systems, application programs and program data stored in random access memory (RAM).

Computer 100 may also include a variety of interface units and drives for reading and writing data. In particular, computer 100 includes a hard disk interface 116 and a removable memory interface 120 respectively coupling a hard disk drive 118 and a removable memory drive 122 to system bus 114. Examples of removable memory drives include magnetic disk drives and optical disk drives. The drives and their associated computer-readable media, such as a floppy disk 124 provide nonvolatile storage of computer readable instructions, data structures, program modules and other data for computer 100. A single hard disk drive 118 and a single removable memory drive 122 are shown for illustration purposes only and with the understanding that computer 100 may include several of such drives. Furthermore, computer 100 may include drives for interfacing with other types of computer readable media.

A user can interact with computer 100 with a variety of input devices. FIG. 13 shows a serial port interface 126 coupling a keyboard 128 and a pointing device 130 to system bus 114. Pointing device 128 may be implemented with a mouse, track ball, pen device, or similar device. Of course one or more other input devices (not shown) such as a joystick, game pad, satellite dish, scanner, touch sensitive screen or the like may be connected to computer 100.

Computer 100 may include additional interfaces for connecting devices to system bus 114. FIG. 13 shows a universal serial bus (USB) interface 132 coupling a video or digital camera 134 to system bus 114. An IEEE 1394 interface 136 may be used to couple additional devices to computer 100. Furthermore, interface 136 may be configured to operate with particular manufacturer interfaces such as FireWire developed by Apple Computer and i.Link developed by Sony. Input devices may also be coupled to system bus 114 through a parallel port, a game port, a PCI board or any other interface used to couple an input device to a computer.

Computer 100 also includes a video adapter 140 coupling a display device 142 to system bus 114. Display device 142 may include a cathode ray tube (CRT), liquid crystal display (LCD), field emission display (FED), plasma display or any other device that produces an image that is viewable by the user. Additional output devices, such as a printing device (not shown), may be connected to computer 100.

Sound can be recorded and reproduced with a microphone 144 and a speaker 146. A sound card 148 may be used to couple microphone 144 and speaker 146 to system bus 144. One skilled in the art will appreciate that the device connections shown in FIG. 13 are for illustration purposes only and that several of the peripheral devices could be coupled to system bus 114 via alternative interfaces. For example, video camera 134 could be connected to IEEE 1394 interface 136 and pointing device 130 could be connected to USB interface 132.

Computer 100 can operate in a networked environment using logical connections to one or more remote computers or other devices, such as a server, a router, a network personal computer, a peer device or other common network node, a wireless telephone or wireless personal digital assistant. Computer 100 includes a network interface 150 that couples system bus 114 to a local area network (LAN) 152. Networking environments are commonplace in offices, enterprise-wide computer networks and home computer systems.

A wide area network (WAN) 154, such as the Internet, may also be accessed by computer 100. FIG. 13 shows a modem unit 156 connected to serial port interface 126 and to WAN 154. Modem unit 156 may be located within or external to computer 100 and may be any type of conventional modem such as a cable modem or a satellite modem. LAN 152 may also be used to connect to WAN 154. FIG. 13 shows a router 158 that may connect LAN 152 to WAN 154 in a conventional manner.

It will be appreciated that the network connections shown are exemplary and other ways of establishing a communications link between the computers can be used. The existence of any of various well-known protocols, such as TCP/IP, Frame Relay, Ethernet, FTP, HTTP and the like, is presumed, and computer 100 can be operated in a client-server configuration to permit a user to retrieve web pages from a web-based server. Furthermore, any of various conventional web browsers can be used to display and manipulate data on web pages.

The operation of computer 100 can be controlled by a variety of different program modules. Examples of program modules are routines, programs, objects, components, data structures, libraries, etc. that perform particular tasks or implement particular abstract data types. The present invention may also be practiced with other computer system configurations, including hand-held devices, multiprocessor systems, microprocessor-based or programmable consumer electronics, network PCS, minicomputers, mainframe computers, personal digital assistants, mobile telephones and the like. Furthermore, the invention may also be practiced in distributed computing environments where tasks are performed by remote processing devices that are linked through a wireless or wired communications network. In a distributed computing environment, program modules may be located in both local and remote memory storage devices.

As previously discussed, various inventive methods may be embodied as computer readable instructions stored on a computer readable medium/media such as a floppy disk, CD-ROM, removable storage device, hard disk, system memory, embedded memory or other data storage medium. The computer readable medium stores computer executable components, or software modules. More or fewer software modules may alternatively be used. Each component may be an executable program, a data link library, a configuration file, a database, a graphical image, a binary data file, a text data file, an object file, a source code file, or the like. When one or more computer processors execute one or more of the software modules, the software modules interact to cause one or more computer systems to perform according to the teachings of the present invention.

Toothbrush/Probe Environment

Figure 14:
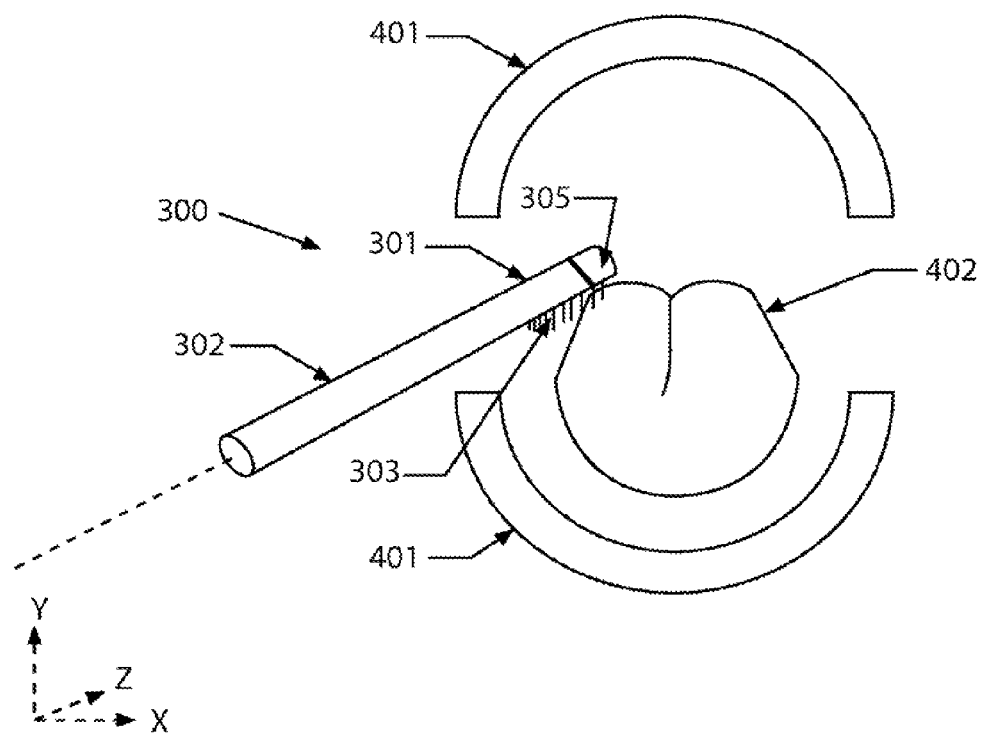
FIG. 14 illustrates a representative oral care implementation environment embodying one or more aspects of the invention.
Figure 15:
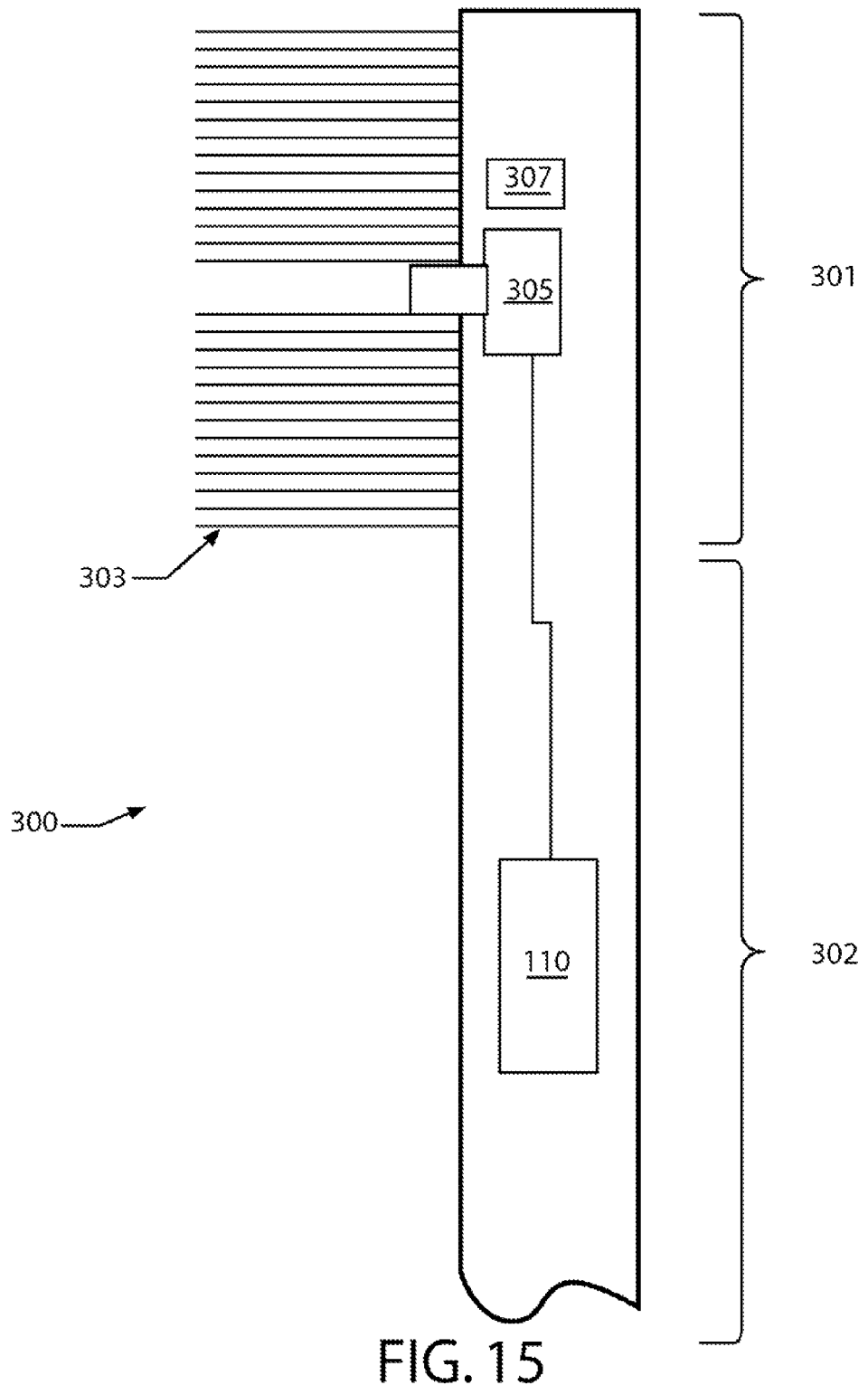
FIG. 15 is a schematic representation of a toothbrush/probe embodying one or more aspects of the invention.

As illustrated in FIGS. 14 and 15, the user holds the toothbrush/probe 300 and may brushes his/her teeth 401. On occasion, the user may also brush his/her tongue 402. In operation, the toothbrush/probe 300 may obtain various samples using the diagnostic sensor system 305, and in conjunction with the processor 110 to provide for home use by a consumer to monitor, for example, an ongoing oral treatment regimen by determining relative amounts of deposited agents over time. Such toothbrush/probe devices may be used alone or may alternatively be incorporated into toothbrushes or other oral care devices. Users of the device will advantageously be able to obtain quick results to allow effective monitoring of an oral care regimen. Also, users can respond to such results by adapting the regimen appropriately (e.g., by brushing and/or flossing more often or for a longer period).

Referring to FIGS. 14 and 15, the toothbrush/probe 300 has a head 301 and handle 302. The head 301 may include an oral care region comprising one or more tooth cleaning elements 303, such as bristles. The head 301 and handle 302 may be made from a desired material, such as rigid plastics, resins, rubber, etc., such as polypropylene.

As used herein, the term "tooth cleaning elements" or "cleaning elements" includes any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members.

Toothbrush/probe 300 may include a lighting device 307, such as light-emitting diode (LED), or any other desired form of visual output to provide the electromagnetic frequency for spectrum analysis. For example, lighting device 307 may be an Organic LED that can be tuned to provide a desired characteristic such as color, temperature, intensity, electromagnetic wavelength and the like. OLED technology can be embedded into the toothbrush molding, or can be applied to the surface of the toothbrush body. It should be understood by those skilled in the art that the present invention is not limited to any particular type of lights used in the analysis.

The toothbrush/probe 100 may also include a diagnostic sensor system or bio-sensor system 305. The diagnostic sensor system 305 may include one or more individualized sensors or sensor suites to detect various characteristics according to the described methods including providing light for Near-Infrared (Near-IR) spectroscopy or Ultraviolet (UV) spectroscopy. For example, the diagnostic sensor system 305 may include a sensor configured the presence of certain chemicals or actives in the sample, or any other desired characteristics as described herein.

The sensor system 305 described above may be electrically or communicatively coupled to a central processor 110, for example or an on-board processor. The processor 110 generally handles the information gathered by the sensor system 305 and reports an analysis of that information to the user, to help inform the user of the conditions within his/her mouth. For example, the toothbrush/probe 300 processor 110 may report that it has detected a level of Triclosan in the upper-left portion of the user's teeth.

The following examples are set forth as representative of the present invention. These examples are not to be construed as limiting the scope of the invention as these and other equivalent embodiments will be apparent in view of the present disclosure.

EXAMPLE 1

A study was performed to evaluate and develop rapid analytical methods for direct quantification of active delivery on oral surface models, to validate the use of Near-IR spectroscopy to analyze Triclosan delivery on saliva-coated hydroxyapatite disks, and correlate results with conventional solvent extraction methodology. Near IR Spectroscopy measures vibrations of molecules. The —CH, =NH, —OH, and —SH signals are strong. Overtones in Near-IR display unique combination bands for analysis. Instrument allows for measurement over a greater surface area.

Human saliva was collected and measured. Parafilm-stimulated whole saliva was collected from healthy adults in sterile centrifuge tubes. The whole saliva was clarified by centrifuging for 10 minutes at 10,000 RPM (Sorvall SS-34 rotor). The saliva supernatant was sterilized under UV light for a minimum of 45 minutes. The clarified sterilized saliva was then ready for use in pellicle formation. Pellicle formation on HAP involved incubating HAP disks (0.5" diameter× 0.05" thick, Clarkson Chromatography, Inc.) with 1 ml clarified sterilized saliva in a 14 ml sterile round bottom tube for 20 hours in a 37° C. shaking water bath. The saliva was removed by aspiration. The saliva-coated HAP disks were incubated with 1 ml of Triclosan treatment solutions for 5 minutes (in triplicate). The treated disks were washed 3 times with DI water, the dried for 1 hour in a 37° C. oven. The treated disks were directly measured by Near-IR, with 3 disks per treatment solution. Each side was measured three times. The disks were also subsequently measured by solvent extraction (using ethanol) and HPLC.

As a result of the study, it was found that Near-IR spectroscopy can be used to directly measure the deposition of Triclosan on scHAP substrates. Also, the developed method can be used to rapidly evaluate the deposition achieved by different active delivery systems.

EXAMPLE 2

Direct Methods of Active Analysis by Near IR and Uv/Vis

1) Analytical Protocol (Sample Preparation & Data Collection)

Blank samples were prepared for all measurements to ensure differentiation of placebo samples from treated samples 2) Wavelength Selection (Performed in Several Ways)

Pure materials were measured as powders or as solutions and the signature minus the blank was measured. The spectral fingerprint of the ingredient of interest was viewed and regions and wavelengths were identified that appear free from interfering components. In some instances, first or second derivative preprocessing was applied to sharpen the separation among ingredients present in a mixture.

Other methods for identification of wavelengths of choice included 1) use of 2-D correlation spectroscopy using other methods such as IR to help define the wavelengths required in both NIR and UV. Using 2-D correlation of data sets that consisted of samples prepared over a range of active concentrations, the regions that change with concentration can be correlated to help make exact band assignments in the Near IR and UV regions using Mid IR to guide these interpretations. 2) Another method for wavelength selection was to the use of simple linear regression methods to find individual bands which were highly correlated to concentration. Once the exact wavelengths were identified, methods of quantitation could be applied, including, but not limited to, peak area method, multiple linear regression and partial least squares regression. 3) A final method for wavelength selection was the use of "Genetic algorithms". This was a method that found the right combination of wavelengths for enhancing the correlation statistics and minimizing regression error using, partial least squares or multiple linear regression analysis.

3) Test Equipment

FOSS™ Dispersive Near ER Model XDS with Rapid Content Accessory (RCA)

Perkin Elmer Lambda 650 UV Vis Spectrophotometer with UV WinLab5 Enhanced Security software. Sampling accessory consists of a L650 Integrating Sphere 60 mm 4) Data Collection In the case of Near IR analysis, the samples were placed on top of the RCA measurement window. The sample was measured using 32 co-added scans from 400 nm to 2500 nm. The average measurement was stored. For HAP disk analysis, each treatment was applied to 3 separate HAP disks. The Near IR measurements were made 3 times on each side for a total of 6 measurements per disk, 18 per each treatment. In order to determine the concentration of deposited active or excipient (such as SLS), the $2^{nd}$ derivative was taken of each spectrum. The peak area was integrated using peak integration software commercially sold by Thermo Galactic. The wavelengths used depended upon the isolated regions identified above. Triclosan includes 1604-1804 nm and/or 2190-2300 nm. For SLS the Near IR regions included 1192-1298; 1626-1814 and 2250-2400 nm. In the UV, the region used for Active analysis included the region from 200-500 nm. The average results for each disk were evaluated to ensure reproducibility between disks with same treatment applied.

In the case of UV analysis, the samples were centrally mounted on a 99% reflective Spectralon disk using double sided tape. The sample was measured from 200 to 400 nm at an interval of 1 nm spacing. The UV detection was recorded as % Reflection versus wavelength. The % Reflection was converted into Kubelka-Monk absorbance units which were correlated to concentration. The average of n replicates were then subtracted from the average of n placebo disks. The $2^{nd}$ Derivative using a 10 point smoothing function was taken. At that point either peak area of the band of interest was performed, or PLS Regression from 262 nm-324 nm was used.

Overall Approaches for the above examples therefore evaluated analytical techniques using Triclosan as a model oral active agent. Analyses were conducted using Near-IR and UV spectroscopy. Various methods of data manipulation were employed, including peak area determination, multiple liner regression (MLR), partial least squares (PLS) (chemometrics). In these experiments, new analytical techniques were correlated with conventional solvent extraction methodology.

The methods described and developed herein are applicable in the characterization of new agents such as oral active agents. The methods are useful in the development of enhanced methods for the delivery and retention of active agents on oral surfaces. The methods are applied where it is necessary or useful to quantify the amount of deposition (uptake) onto the surface. In the experimental examples described above, the methods utilized hydroxyapatite (HAP) disks as model hard tissue substrates. The methods developed overcome various limitations of the conventional solvent extraction method, including the indirect nature of the analysis, the time consuming steps involved, and the lack of information about potential agent-substrate interactions.

The Near-IR analytical technique, based on measuring the vibration of molecules, has the advantages of providing direct and rapid analysis of solid and liquid substrates and finished products, as well as good speciation of agents such as oral active agents in a mixture. Thus, multi-component analysis is possible (e.g., of a mixture such as triclosan and sodium lauryl sulfate).

The UV analytical technique, based on electronic transitions between energy levels, also provides direct and rapid analysis of solid and liquid substrates. Various advantages and benefits are associated with the direct analytical methods described herein, including the ability to characterize agents such as oral active agents in their native state in a dentifrice matrix, increased throughput, and expedited new formula screening and analytical testing.

The foregoing detailed description has set forth various embodiments of the devices and/or processes via the use of block diagrams, flowcharts, and examples. Insofar as such block diagrams, flowcharts, and examples contain one or more functions and/or operations, it will be understood by those within the art that each function and/or operation within such block diagrams, flowcharts, or examples can be implemented, individually and/or collectively, by a wide range of hardware, software, firmware, or any combination thereof. In one embodiment, the aspects may be implemented via Application Specific Integrated Circuits (ASICs). Those, however, skilled in the art will recognize that the embodiments disclosed herein, in whole or in part, can be equivalently implemented in standard Integrated Circuits, as a computer program running on a computer, as a program running on a processor, as firmware, or as virtually any combination thereof and that designing the circuitry and/or writing the code for the software or firmware would be well within the skill of one of ordinary skill in the art in light of this disclosure.

We claim:

1. A method for measuring deposition of an oral agent from a dentifrice on a substrate, the method comprising:
    (a) contacting the substrate with the oral agent to deposit an amount of the oral agent thereon, wherein the substrate is coated with saliva and
    (b) analyzing the substrate using Near-Infrared Near-IR) spectroscopy or an Ultraviolet (UV) spectroscopy probe contained within a toothbrush
wherein a wavelength used in step (b) is specific to said oral agent and wherein a reference signal of the dentifrice without the oral agent is subtracted from the analysis to provide an amount for the oral agent.

2. The method of claim 1, wherein the oral agent is triclosan.

3. The method of claim 1, further comprising, after step (a) and prior to step (b), drying an oral agent-containing substrate obtained in step (a).

4. The method of claim 3, wherein the oral agent-containing substrate obtained in step (a) is dried to a predetermined water concentration.

5. The method of claim 1, wherein in (b) analysis of the substrate is by using Ultraviolet spectroscopy.

6. The method of claim 5, wherein the oral agent is triclosan and the substrate comprises hydroxyapatite (HAP).

7. The method of claim 1, wherein the substrate is analyzed using a Near-IR spectroscopy instrument or a UV spectroscopy instrument having a solid measurement accessory.

8. The method of claim 7, wherein the substrate is analyzed using a Near-IR spectroscopy instrument and the solid measurement accessory is a rapid content analyzer (RCA).

9. The method of claim 7, wherein the substrate is analyzed using a UV spectroscopy instrument and the solid measurement accessory is an integrating sphere accessory.

10. The method of claim 9, further comprising, after step (a) and prior to step (b), positioning an oral agent-containing substrate obtained in step (a) on a reflective disk plate in the integrating sphere accessory.

11. The method of claim 1, further comprising, after step (b), applying a mathematical method to obtain quantitative information from a Near-IR spectrum or a UV spectrum generated in step (b).

12. The method of claim 11, wherein the mathematical method is selected from the group consisting of first and second derivative, peak area integration, partial least squares regression (PLS), Kubelka-Munk conversion, and spectral subtraction.

13. One or more computer readable media storing executable instructions that, when executed, cause a data processing system to perform a method comprising steps of: analyzing a Near-IR spectrum or a UV spectrum generated according to the method of claim 1 using a mathematical method is selected from the group consisting of first and second derivative, peak area integration, partial least squares regression (PLS), Kubelka-Munk conversion, multiple linear regression, and spectral subtraction.

14. The computer readable media of claim 13, wherein, the method comprises performing spectral subtraction from the Near-IR spectrum to obtain a resolved, Near-IR spectrum for the deposited oral agent, determining the second derivative of the resolved, Near-IR spectrum, and integrating the area under one or more relevant peaks of the second derivative of the resolved, Near-IR spectrum.

15. The computer readable media of claim 13, wherein the method comprises performing Kubelka-Munk conversion to convert the UV spectrum to a corresponding UV absorbance spectrum, performing spectral subtraction from the corresponding UV absorbance spectrum to obtain a resolved, corresponding UV absorbance spectrum fox the deposited oral agent, determining the second derivative of the resolved, corresponding UV absorbance spectrum, and integrating the area under one or more relevant peaks of the second derivative of the resolved, corresponding UV absorbance spectrum.

\* \* \* \* \*